US00PP07888P

United States Patent [19]

Marciel

[11] Patent Number: Plant 7,888

[45] Date of Patent: Jun. 23, 1992

[54] TEA ROSE NAMED DEVILK

[75] Inventor: Stanley G. Marciel, Aptos, Calif.

[73] Assignee: DeVor Nurseries, Inc., Watsonville, Calif.

[21] Appl. No.: 615,156

[22] Filed: Nov. 19, 1990

[51] Int. Cl.[5] ..... A01H 5/00

[52] U.S. Cl. ..... Plt./20

[58] Field of Search ..... Plt. 16, 17, 20

*Primary Examiner*—James R. Feyrer

*Attorney, Agent, or Firm*—Charles W. Rummler

[57] ABSTRACT

A new and distinct tea rose variety particularly distinguished by its continuous and profuse production of flowers of a relatively large size and of an Orange color carried singly on long, strong upright stems of a plant having a vigorous upright growth habit and an abundant production of foliage of relatively large size.

1 Drawing Sheet

BACKGROUND OF THE NEW PLANT

This new tea rose originated as a seedling hybrid produced by me at my nursery at Pleasanton, Calif. by my crossing the variety 'Sonia' (U.S. Plant Pat. No. 3,095) with pollen from the variety 'Prominent' (U.S. Plant Pat. No. 3,380) and the present seedling of that hybridization was selected by me for propagation because of the very Light Red coloration of its bloom and the sturdy long stemmed upright growth habit. Propagation of this selected seedling was done by me at Pleasanton, Calif. by budding with such success that under my direction, propagation of this new plant was continued through several successive generations which proved conclusively that the novel characteristics of the selected seedling would hold true from generation to generation and appeared to be firmly fixed and its homogeneity could be assured. This new plant is now being propagated by budding at my nursery at Wasco, Calif.

DESCRIPTION OF THE DRAWING

This new tea rose plant is illustrated by the accompanying full color photographic drawing which shows flowers of the new variety in several stages of maturity and with a color rendition that is as nearly true as that herein specified as is reasonably possible to obtain by conventional photographic procedures.

DESCRIPTION OF THE NEW VARIETY

The following is a detailed description of my new tea rose based upon observation of plants grown in greenhouses at Pleasanton, Calif. with the color designations being according the The R.H.S. Colour Chart published by The Royal Horticultural Society of London, England.

THE PLANT

Origin: Seedling.

Parentage:

*Seed parent.*—'Sonia', U.S. Plant Pat. No. 3,095.

*Pollen parent.*—'Prominent', U.S. Plant Pat. No. 3,380.

Classification:

*Botanic.*—Hybrid Tea Rose.

*Commercial.*—Greenhouse Rose.

Form: Upright bush of rounded and spreading shape.

Growth habit: Vigorous, strong and upright.

Height: About 55 cm.

Main stem:

*Length.*—About 45 to 52 cm. from the last flower cut.

Branching character: Free branching.

Foliage:

*Quantity.*—Abundant.

*Number of leaves.*—From 3 to 5 from last flower cut.

*Size.*—About 75 mm. long and 50 mm. wide.

*Shape.*—Generally oval.

*Leaflets.*—Number: 3 or 5. Size: About 43 mm. long and 28 mm. wide, in average. Shape: Ovate with denticulate margin. Texture: Leathery. Aspect: Glossy. Color: Upper side — Yellow Green 146-A. Under side — Yellow Green 148-B, with tinges of Greyed Purple 185-C. Stipules: Hairy adnate. Pedioles: 1 mm. Rachis: 72 mm. for 5 part leaf and 43 mm. on 3 part leaf.

Calyx:

*Shape.*—Funnel-shaped.

*Size.*—Medium.

*Splitting.*—Calyx does not split.

*Aspect.*—Smooth.

Peduncle of flower stem:

*Length.*—About 107 to 112 mm.

*Character.*—Slender and erect.

*Color.*—Yellow Green 144-B.

THE FLOWER

Blooming habit: Continuous and profusely the year around; blooming freely under greenhouse conditions.

Size of bloom: Large.

*Diameter.*—(When ½ open) about 52 mm. by 40 mm.

*Depth.*—37 mm.

Borne: Singly.

Shape:

*When bloom first opens.*—High center.

*When bloom matures.*—Nicely imbricated.

Petalage:

*Number.*—19.

*Number of florets.*—2.

*Arrangement.*—Imbricated.

*Form.*—Pointed spoon shaped with ruffled margin.

*Texture.*—Soft.

*Appearance.*—Velvety.

*Color* (*year around*).—Outer petals body — Red 43-B and base of Yellow Green 154-C. Reverse side body — Red 43-C and base of Yellow Green 154-D. Inside Petals — Red 41-A and base of Yellow 2-B. Reverse side — Red and base of Yellow 3-C.

*Petaloids.*—Number: 2. Size: About 15 mm. Color: Red 45-C with base of Yellow 6-C.

Peduncle:

*Length.*—About 107 to 112 mm.

*Color.*—Yellow Green 144-B.

*Character.*—Upright and sturdy.

Discoloration after full bloom: Discolors from Red 43-B to Red 48-C.

Persistence: The flowers hang on and dry.

Disease resistance: Resistant to mildew, rust and black spots as observed at Watsonville, Calif.

Fragrance: Strong musk-like.

Lasting quality: Long lasting on plant and as a cut flower.

THE REPRODUCTIVE ORGANS

Stamens:

*Number.*—120 to 123.

*Arrangement.*—Introrse.

*Anthers.*—Size: 2 mm. Color: Yellow Orange 16-A.

*Filaments.*—Length: About 8 mm. Color: Greyed Purple 185-C with Yellow 7-C at ends.

*Pollen.*—Color: Yellow Orange 18-A.

Pistils:

*Number.*—39.

*Styles.*—Length: 9 mm. Color: Green White 157-C.

*Stigmas.*—Color: Yellow 11-B.

Character of the ovaries: Oval, slightly flattened with a covering of silvery hairs.

THE FRUIT

Fertility: The fruit is fertile.

Shape: Round.

Color at maturity: Yellow Orange 23-B.

I claim:

1. The new and distinct tea rose variety substantially as herein shown and described, particularly characterized by its profuse and continuous production of large flowers having a generally Orange coloration, the plant being further distinguished by its vigorous free branching growth habit and abundant foliage.

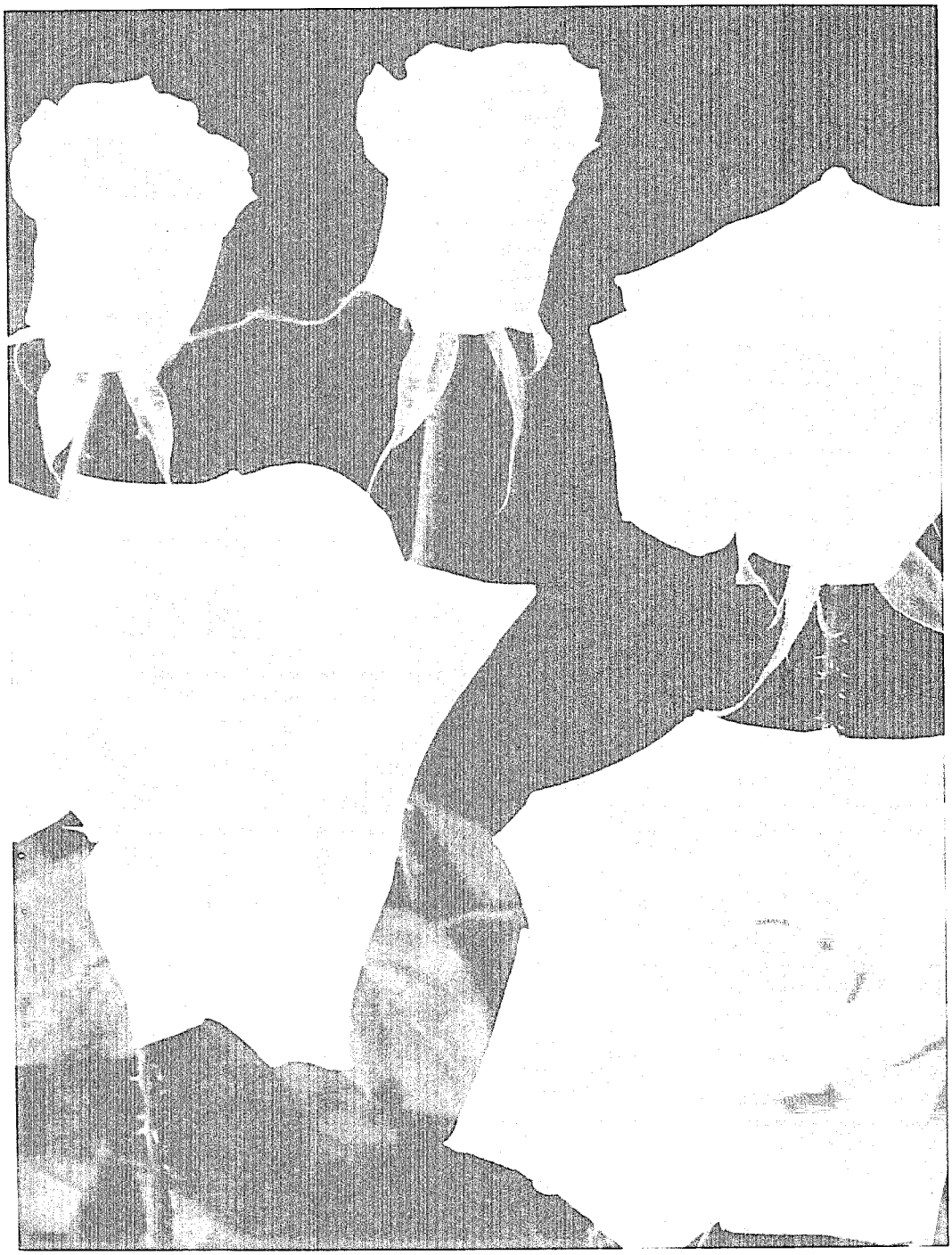

* * * * *